United States Patent [19]

Jones et al.

[11] Patent Number: 4,746,505
[45] Date of Patent: May 24, 1988

[54] TECHNETIUM RADIODIAGNOSTIC FATTY ACIDS DERIVED FROM BISAMIDE BISTHIOL LIGANDS

[75] Inventors: Alun G. Jones, Newton Centre; John Lister-James, Wellesley; Alan Davison, Needham, all of Mass.

[73] Assignees: President and Fellows of Harvard College, Cambridge; Children's Medical Center Corp., Boston; Massachusetts Institute of Technology, Cambridge, all of Mass.

[21] Appl. No.: 727,582

[22] Filed: Apr. 26, 1985

[51] Int. Cl.$^4$ .................... A61K 43/00; A61K 49/02; A61K 49/00; C07C 149/23
[52] U.S. Cl. ........................ 424/1.1; 534/14; 260/402.5; 422/61; 424/9
[58] Field of Search ............... 534/14, 10; 424/1.1, 424/9; 260/401, 402.5; 422/61

[56] References Cited

U.S. PATENT DOCUMENTS

| | | | |
|---|---|---|---|
| 4,434,151 | 2/1984 | Byrne et al. | 424/1.1 |
| 4,444,690 | 4/1984 | Fritzberg | 534/14 |
| 4,615,876 | 10/1986 | Troutner et al. | 424/1.1 |
| 4,673,562 | 6/1987 | Davison et al. | 424/1.1 |

OTHER PUBLICATIONS

Davison et al., Inorg. Chem., 20:6, pp. 1629-1632, (1981).
Fritzberg et al., J. Nucl. Med. 22:258-263, (1982).
Jones, A. et al., "Chemical and In Vivo Studies of the Anion Oxo [N,N'-Ethylenebis(2-Mercaptoacetimido)]-Technetate(V)", J. Nucl. Med., 23:9 pp. 801-809 (82).
Fritzberg, A. et al., "Synthesis & Biological Eval. of Tc-99m N,N'-Bis(Mercaptoacetyl)-2,3-... o-Iodohippurate", J. Nucl. Med., 23:7, pp. 592-598 (1982).
Fritzberg, W. P. et al., "Tc-99m Complexes Based on Diamide Dimercaptide Donor Groups (N$_2$S$_2$)... Renal Function Agents", J. Nucl. Med., 23:5, p. 17 (1982).
Fritzberg, A. R. et al., "Chemical & Biological Studies of Tc-99m-N,N'-Bis(Mercaptoacetamido) . . . I-131-Hippuran", J. Nucl. Med., 22:6, p. 52 (1981).
Fritzberg, A. R. et al. "Renal Transport Mechanism Studies of Tc-99m-N,N'-Bis(Mercaptoacetamido)Ethylenediamine", J. Nucl. Med., 22:6, p. 51 (1981).
Klingensmith, W. C. et al., "Clinical Comparison of Tc-99m-N,N-Bis(Mercaptoacetamido)ethylenediamine (Tc-DADS) . . . Renal Tubular Function" J. Nucl. Med, 22:6, p. 38 (81).
Klingensmith, W. C. et al., "Clinical Evaluation of Tc-99m,N,N'-Bis(Mercaptioacetyl)2,3-Diaminopropanoate . . . for I-131-Hippuran" J. Nuc. Med. 24:5, p. 80 (1983).
Byrne, E. et al. "Technetium-99m Bifunctional Chelating Agent . . . to Technetium", Society of Nuc. Med., 30th Annual Meeting, Jun. 7-10, 1983.
Subramanian, G. et al., "An Evaluation of 16 New Tc-99m Compounds for Renal Tubular Excretion Studies", J. Nucl. Med. 24:5, p. 80 (1983).
Costello, C. E. et al "The Investigation of Radiopharmaceutical Components by Fast Atom Bombardment Mass Spectrometry: . . . CO$_2$DADS", J. Nucl. Med. 23:353-55 (1983).
Davison, A. et al., "A Tetradentate Ligand Designed Specifically to Coordinate Technetium", J. Nucl. Med., 20:6, p. 641 (1979).
Jones, A. et al., "Oxotechnetium Complexes Containing TcON$_2$S$_2$ Cores", Fourth International Symp. on Radiopharmaceutical Chem. p. 333 Aug. 23-27, 1982).
Davison, A. et al., "A Series of Oxotechnetium (+5)Chelate Complexes Containing a TcOS$_2$N$_2$ Core", J. Nucl. Med., 22:6, pp. 57-58 (1981).

Primary Examiner—John F. Terapane
Assistant Examiner—J. E. Thomas
Attorney, Agent, or Firm—Sewall P. Bronstein; George W. Neuner; Ronald I. Eisenstein

[57] ABSTRACT

A bisamide-bisthiol ligand containing fatty acid substituted thiol useful for producing Tc-labelled radiodiagnostic imaging agents is described. The ligand forms a complex with the radionuclide $^{99m}$Tc suitable for administration as a radiopharmaceutical to obtain images of the heart for diagnosis of myocardial disfunction.

27 Claims, No Drawings

TECHNETIUM RADIODIAGNOSTIC FATTY ACIDS DERIVED FROM BISAMIDE BISTHIOL LIGANDS

This invention was made with government support and the United States government has certain rights in the invention.

FIELD OF THE INVENTION

The present invention relates to radiodiagnostic agents and, more particularly, to ligands useful as intermediates for producing $^{99m}$Tc-labeled radiodiagnostic agents, novel $^{99m}$Tc-labeled radiodiagnostic agents, kits for preparing such $^{99m}$Tc-labeled radiodiagnostic agents and methods for using such $^{99m}$Tc-labeled radiodiagnostic agents, particulary to bisamide-bisthiol ligands comprising a carboxyalkylthio moiety.

BACKGROUND OF THE INVENTION

The radionuclide $^{99m}$Tc has excellent physical decay characteristics for application in nuclear medicine, and is readily available in a radionuclide generator system. More than 80% of all diagnostic nuclear medicine procedures in the United States now involve the administration of radiopharmaceuticals labeled with this radioisotope. The 140 keV gamma ray emitted in 89% of all disintegrations of this metastable nuclear state is well matched to the properties of modern scintillation camera systems, and the level of nonpenetrating radiation following decay gives a low absorbed radiation dose to the recipient. In turn, this means that large amounts of radioactivity can be administered leading to more reliable statistics in quantitative studies. Thus, serial monitoring also is possible with technetium. Additionally, the halflife of 6.02 hours is better matched to the length of most current studies.

The ability to assess pathologically altered myocardial morphology and function is of paramount importance given the incidence of heart disease in the population. The current methods of choice in routine nuclear medicine for studying the patency of cardiac structure and function are $^{201}$Tl as thallous chloride for perfusion, $^{99m}$Tc-labeled erythrocytes for gated wall motion and ejection fraction determinations, and $^{99m}$Tc-pyrophosphate for infarct-avid imaging. None of these agents, however, are useful for the study of the primary energy source of the heart under aerobic physiological conditions: i.e. the oxidation of fatty acids. See Bing et al., *Am. J. Med.* 16:504 (1954).

Over the last decade, considerable effort has been directed toward the synthesis of fatty-acid derivatives, labeled with gamma and positron-emitting radionuclides, in order to provide a non-invasive means of assessing regional myocardial metabolism and its pathology-related variation. See Machulla, "Radioactive Labelling of Fatty Acids for Metabolic Studies" in Lambrecht et al. (eds.), *Application of Nuclear and Radiochemistry*, Pergamon Press, New York (1982) at p. 325.

Much emphasis has been placed on iodinated derivatives, in which omega-substitution has been found to cause least deviation from normal biodistribution. However terminally iodinated fatty acids give high blood (background) levels because of their rapid degradation to free iodide. To overcome this problem, the use omega-iodophenyl substituted fatty acids (Machulla et al., *Eur. J. Nucl. Med.* 5:171 (1980)) was tried. These derivatives are metabolized to iodobenzoic or iodo- phenylacetic acid which is then rapidly excreted through the kidneys. Nevertheless, omega-$^{123}$I-heptadecanoic acid has been used in the clinical assessment of regional myocardial function in conjunction with an involved background-subtraction procedure. See Freundlieb et al., *J. Nucl. Med.* 21:1043 (1980).

Since $^{99m}$Tc has near ideal physical characteristics for external imaging, several attempts have been made to prepare $^{99m}$Tc-labelled fatty acids. Eckelman (Eckelman et al., *J. Pharm. Sci.* 64:704 (1975) and Karesh et al., *J. Pharm. Sci.* 66:225 (1977)) and Loberg (Loberg et al., *J. Nucl. Med.*, 20:1181 (1979)) prepared several fatty acids omega-substituted with iminoacetate-type ligands. Fritzberg (Fritzberg et al., *J. Lab. Comp. Radiopharm.* 18:52 (1981)) prepared a hexa-thio ligand derivative and Livni (Livni et al., *Radiopharm. II* p. 487 (1979)) prepared some mercaptoacetate derivatives. Each of these ligands formed $^{99m}$Tc complexes but none showed the desired myocardial specificity. The preparation of fatty acid derivatives labeled with $^{99m}$Tc having high myocardial specificity is highly desirable.

Oxotechnetium (+5) bisamido bisthiolato ($N_2S_2$) anion complexes have been reported as kidney imaging agents. See U.S. patent application Ser. No. 524,888, now U.S. Pat. No. 4,673,562, filed Aug. 19, 1983 and Jones et al., *J. Nucl. Med.* 23:801 (1982). The anion, oxo[N,N'-ethylenebis(2-mercapto-acetamido)]technetate (+5), i.e. [TcO(ema)]$^-$, is stable not only in vitro but also in vivo at both carrier-added (CA) and no-carrier-added (NCA) concentrations.

J. W. Brodack disclosed the complex $^{99m}$Tc-oxo[N,N'-ethylene-bis(2-mercapto)-[2'-(11-carboxyundecyl)]thio-acetamido]-technetate (+5), i.e. $^{99m}$TcO(Undec)ema, in his doctoral thesis "Applications Of High-Pressure Liquid Chromatography In The Study Of Technetium Chemistry" submitted May, 1983, Massachusetts Institute of Technology. This compound was later tested for myocardial imaging in mice, however, a significant problem was encountered in the continuously high blood levels (6–8%/g) over the first 30 min, resulting in poor heart:blood ratios (0.8:1 at 5 min; 0.3:1 at 30 min). In addition, the relatively high kidney activity observed even at 5 min. post-injection suggests rapid metabolism to the TcO(ema)$^{-1}$ complex which is known to undergo rapid renal excretion.

Thus, a $^{99m}$Tc-labelled ligand useful for studying the heart under aerobic physiological conditions is still being sought.

SUMMARY OF THE INVENTION

The present invention provides bisamide, bisthiol fatty acid-containing compounds that form complexes with technetium, thereby producing novel radioimaging agents.

The compounds of the present invention are typically represented by the following structural formulae:

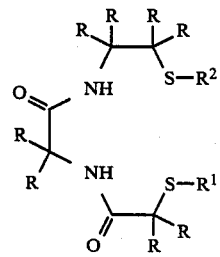

I

-continued

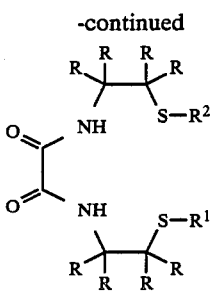

and

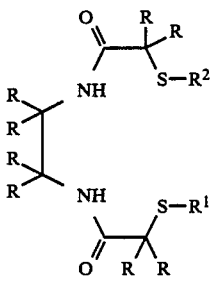

wherein each R is independently selected from the group consisting of hydrogen, substituted or unsubstituted lower alkyl, substituted or unsubstituted lower alkoxy, or —COR$^4$ where R$^4$ is selected from substituted or unsubstituted lower alkoxy, or two R's can be combined to form a lower alkylidene group or a hydrocarbon ring; and R$^1$ and R$^2$ are independently selected from hydrogen, a thiol protecting group and a C$_{14}$ to C$_{24}$ fatty acid group; with the proviso that one of R$^1$ and R$^2$ must be a fatty acid group and the other can not be a fatty acid group; and salts thereof.

The compounds of formulae I, II and III can be complexed with technetium to form the following complex species:

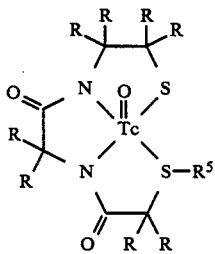

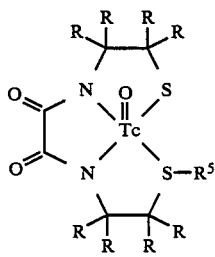

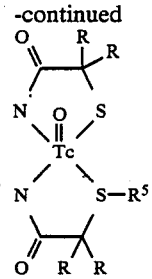

where R is as defined above and R$^5$ is a fatty acid group as defined above for R$^1$ and R$^2$. The complexes of formulae IV, V, and VI form stereo isomers, i.e. they can appear as two diastereomers each diastereomer consisting of a pair of enantiomers. The diastereomers can be separated by high pressure liquid chromatography (HPLC).

These complexes when labelled with $^{99m}$Tc are concentrated in those organs that use fatty acid for energy, e.g. the heart muscle tissue, etc. Thus, the Tc-labelled complexes of the present invention are useful for, among other things, radioimaging the heart. Advantageously, the degradation product of these Tc-labelled complexes is the Tc-labelled N$_2$S$_2$ core complex or a 2-substituted acetate derivative thereof, which is rapidly excreted from the body, thereby minimizing the radiation dose to the patient.

The present invention also provides kits for producing technetium-99m complexes of the type illustrated by formulae IV, V and VI. The kits typically comprise bisamide-bisthiol compounds of the type illustrated by formulae I, II and III and a reducing agent for pertechnetate in a sealed, sterilized container. Preferably, the kits comprise lyophilized bisamide-bisthiol compounds containing a hydrophilic thiol protecting group which permits ready reconstitution with aqueous solutions having a pH in the range of about 5 to about 8.

DETAILED DESCRIPTION OF THE INVENTION

In accord with the present invention, bisamide, bisthiol compounds capable of complexing with technetium and containing a thiol-substituted fatty acid group having 14 to 24 carbon atoms such as compounds of the type having formulae I, II and III are useful for preparing technetium complexes of the type having formulae IV, V and VI. The technetium complexes of the present invention are useful as radiodiagnostic agents, particularly for diagnosing abnormalities of the cardiovascular system.

One of R$^1$ or R$^2$ is hydrogen or any known thiol protecting group. Some examples of such groups are lower alkylaminocarbonyl such as ethylaminocarbonyl, lower alkanoylaminomethyl, aroylaminomethyl, t-butyl, acetamidomethyl, arylmethyl such as triphenylmethyl (trityl) and diphenylmethyl, aroyl such as benzoyl, aryloxycarbonyl such as phenoxycarbonyl, aryl-loweralkoxylcarbonyl, preferably arylmethoxycarbonyl such as benzyloxycarbonyl, and lower alkoxycarbonyl such as t-butoxycarbonyl. Preferred thiol protecting groups include trityl, t-butyl, diphenylmethyl, acetamidomethyl and benzoyl.

The remaining R$^1$ or R$^2$ (i.e. R$^5$ in the technetium complex) not accounted for supra is a C$_{14}$ to C$_{24}$ fatty acid group. As used herein, the term "fatty acid" includes both saturated and unsaturated carboxylic acids having an odd or even carbon content, in straight or branched configuration, containing from 14 to 24 carbon atoms. Preferably, there are from 15 to 20 carbon atoms in the fatty acid group, and most preferably, from 16 to 18 carbon atoms. Examples of fatty acids useful herein include: myristic ($C_{14}$); palmitic ($C_{16}$); stearic ($C_{18}$); arachidic ($C_{20}$); lipnoceric ($C_{24}$); palmitoleic ($C_{16}$); oleic ($C_{18}$); and arachidonic ($C_{20}$) acids.

The fatty acids used herein to form the $R^1$ or $R^2$ side chain may be derived from naturally occurring sources or formed synthetically.

The R groups which are substituted on the $N_2S_2$ core may be used to control the liphophilicity of the fatty acid containing complexes of this invention.

The term "lower alkyl" when used in this application designates aliphatic saturated, branched or straight chain hydrocarbon monovalent substitutents containing from 1 to 4 carbon atoms such as methyl, ethyl, isopropyl, n-propyl, n-butyl, t-butyl, and the like. The term "lower alkoxy" designates lower alkoxy substitutents containing from 1 to 4 carbon atoms such as methoxy, ethoxy, isopropoxy, and the like. In the complexes of this invention two adjacent R groups can be combined to form a lower alkylidene group or cyclic group.

The terms substituted lower alkyl or substituted lower alkoxy when used herein include alkyl and alkoxy groups substituted with halogen, (F, Cl, Br, I).

The term "lower alkylidine" as used herein means a hydrocarbon having a terminal $=CR^6R^6$ group where $R^6$ is a methyl or ethyl group and the total number of carbon atoms is from about 3 to about 8. An example of an alkylidine suitable for the practice of this invention is isopropylidene, and the like.

Compounds of formulae I, II and III can be synthesized by following the procedures described in U.S. patent application Ser. No. 524,888 filed Aug. 19, 1983 and by Jones et al., supra, both of which are hereby incorporated by reference, wherein a different thiol protecting group is used for each sulfur atom. One of the sulfur atoms is then deprotected and reacted with a halogenated fatty acid to form the compounds of formulae I, Ii and III.

A typical reaction scheme for a compound of formula III is illustrated below.

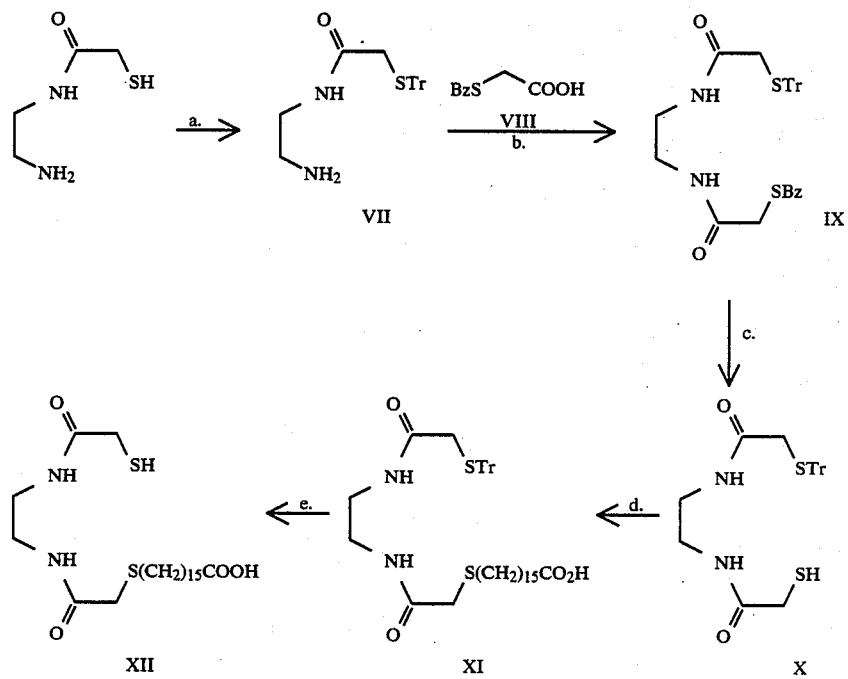

where:
Tr=—$CPh_3$;
Bz=PhCO—;
a. =$Ph_3COH$, $CF_3COOH$;
b. =DCC, HOSu, $CH_2Cl_2$;
c. =NaOMe; MeOH;
d. =Br($(CH_2)_{15}COOH$, NaOMe, MeOH; and
e. =$Et_3SiH$, $CF_3COOH$.

The R groups are not illustrated in the above reaction scheme only for convenience. However, those skilled in the art will appreciate that R groups may be present in any of the forms described above, depending upon the particular reaction conditions used.

Examples of compounds of this invention include:
N,N'-ethylenebis(2-mercapto)[2'-(16-carboxyhexadecyl)thio]acetamide;
N-(2-mercaptoethyl)[2'-(18-carboxyoctadecyl)thioacetyl]glycinamide;
N-(2-mercaptoethyl)-N'-[2-(20-carboxyeicosyl)thioethyl]oxamide;
N-(2-mercaptoethyl)[2'-(15-carboxypentadecyl)thioacetyl]glycinamide
N,N'-ethylenebis(2-mercapto)[2'-(17-carboxyheptadecyl)thio]acetamide;
N-(2-mercaptoethyl)-N'-[2-(19-carboxynonadecyl)thioethyl]oxamide;
N,N'-propylenebis(2-mercapto)[2'-(2'-(16-carboxyhexadecyl)thio]acetamide;
N-(3-mercaptopropyl[3'-(17-carboxyheptadecyl)thiopropionyl]glycinamide; and the like.

The bisamide-bisthiol compounds of this invention also include other compounds capable of complexing technetium with the $N_2S_2$ core to form a pentacoordinate oxotechnetium complex. Examples of additional such compounds are compounds similar to those illustrated by formulae I, II and III but having an extra carbon in the carbon bridge between one or more of the pairs of nitrogen and sulfur atoms. When such an extra carbon is added that portion of the compound when complexed with technetium will form a six membered ring. Examples of such other bisamide-bisthiol compounds include:

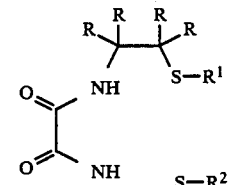
(A)

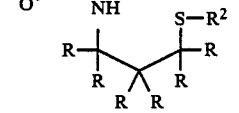
(B)

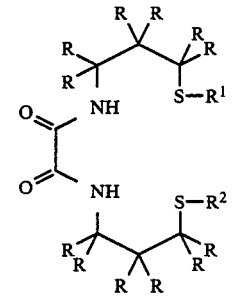
(C)

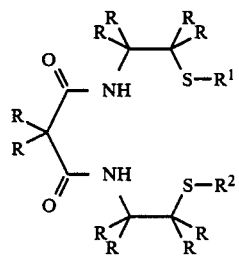
(D)

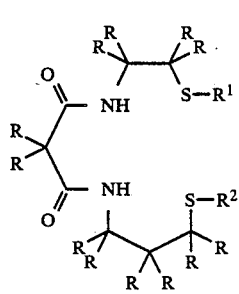
(E)

-continued

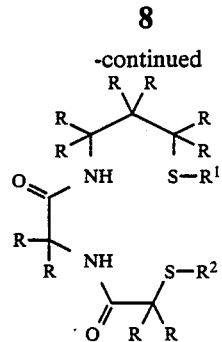
(F)

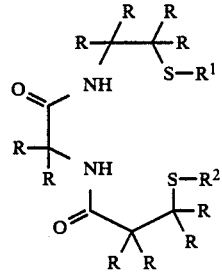
(G)

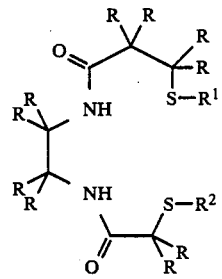
(H)

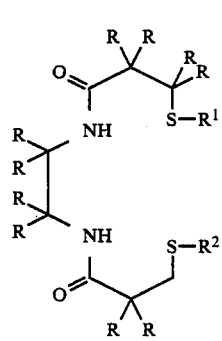
(J)

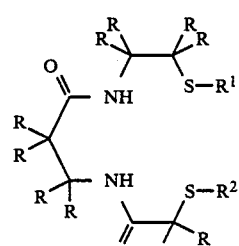
(K)

where the R, $R^1$ and $R^2$ groups are the same as defined above, and salts thereof. These compounds are readily formed by the same techniques described supra by substituting the appropriate propyl derivative in place of the corresponding ethyl derivative in the reaction scheme. Additional such compounds will be readily apparent to those skilled in the art.

Technetium complexes of this invention are formed by reacting the compounds of formulae I, II and III, or A through K, and the like with technetium in the presence of a suitable reducing agent in the conventional manner. For example, the compound is dissolved in a suitable solvent system with a reducing agent and pertechnetate is added. The mixture is heated for a suitable length of time to complete the reaction. Typically, heating in a boiling water bath for about 10 minutes has been found sufficient to obtain good yields of the technetium complex. Addition of a solubilizing agent such as human serum albumin (HSA) can be used to help keep the complex in solution. Examples of reducing agents useful in the practice of this invention include stannous salts such as stannous chloride, sodium dithionite, and ferrous salts such as ferrous sulfate.

Technetium complexes in accord with this invention can also be prepared by ligand exchange with a prereduced technetium complex such as technetium glucoheptanate or the like.

In another embodiment of the present invention, radiopharmaceutical kits preferably comprising, bisamide-bisthiol compounds capable of complexing with technetium typically forming pentacoordinate oxotechnetium complexes are thiol protected with a hydrophilic thiol protecting group such as the acetamidomethyl group and provided with a reducing agent in lyophilized form in a sterilized container or vial. In this form, the lyophilized composition can be readily reconstituted by adding water or an aqueous solution, preferably having a pH in the range of about 5 to 8, more preferably physiological pH. Alternatively, pertechnetate solution may be added, thereby avoiding the use of alcoholic solutions required if other conventional thiol protecting groups are used. The bisamide-bisthiol compounds include N,N'-ethylene-bis(S-(fatty acid)-2-mercaptoacetamide), N,N'-bis(S-(fatty acid)-2-mercaptoethyl) oxamide, and S-(fatty acid)-2-mercaptoacetylglycyl(S-(protected) cysteamine and derivatives substituted with groups such as those illustrated in structural formulae I, II, III, and A through K, etc.

In general, the radiopharmaceutical preparation kits comprise a sterilized unit dose (or multidose) vial containing the purified compound and a reducing agent for technetium, preferably lyophilized. Each dose should consist of a sufficient amount of compound and reducing agent to complex with the required dose, normally less than about 0.5 mCi of $^{99m}Tc$ per kg of body weight of the mammal to be tested. In use, the technetium, preferably as $^{99m}Tc$-pertechnetate in saline is injected aseptically into the vial and the mixture heated for a sufficient time to form the labeled complex. After cooling, the resulting radiopharmaceutical preparation is ready for use. The preparation can be injected into the patient in a suitable pharmacological carrier such as physiological saline, HSA, or the like.

In order to obtain high quality images the radiochemical yield of technetium complex should preferably be greater than 70% after reconstituting the lyophilized mixture and labeling. Lower yields will result in a poorer image quality and undesirable purification steps may be required to produce the image quality desired.

In certain cases, substituted derivatives of the bisamide-bisthiol compounds of this invention as illustrated in the above formulae can give a pair of diastereomers when complexed with technetium. That is, the addition of a substituent at a tetrahedral carbon atom will give rise to additional isomers. As aforesaid each diastereomer itself can consist of a pair of enantiomers.

The invention and its advantages will be further illustrated by the examples that follow. Unless otherwise noted all percentages are reported as weight percent and all temperatures are in °C. In addition, the following abbreviations will have the meanings provided in the tabulation below:
Me-methyl
Et-ethyl
iPr-isopropyl
Bu-n-butyl
Ph-phenyl
Ac-acetyl
Tr-triphenylmethyl
Dpm-diphenylmethyl
Su-succinimido
DCC-dicyclohexylcarbodiimide
DCU-dicyclohexylurea
DME-dimethoxyethane
DMF-dimethylformamide
DMSO-dimethylsulfoxide
TLC-thin layer chromatography
MPLC-medium pressure liquid chromatography
HPLC-high pressure liquid chromatography The metastable radionuclide $^{99m}Tc$ as $Na^{99m}TcO_4$ was obtained from a commercial $^{99}Mo$-$^{99m}Tc$ generator. Technetium as aqueous $NH_4^{99m}TcO_4$ (0.4M) was obtained from E. I. duPont deNemours & Company, Billerica, MA.

Distilled water was passed through a Corning 3508B Ultra-High Capacity Inorganic Cartridge, followed by redistillation in a Corning Mega-Pure 1-liter water still.

High pressure liquid chromotography (HPLC) was performed as either of two systems:

System A-Radial-PAK 10 μm C18 cartridge on a Z-module Radial Compression Separation System (Waters Assoc.); solvent A 0.05M aqueous ammonium sulfate; solvent B methanol; flow rate 3 ml/min; initial conditions 100% solvent A; upon injection a 10 min. linear gradient to 5%A, 95%B was applied followed by a 5 min. hold followed by return to initial conditions over 1 min. and a subsequent hold at initial conditions for 4 min.

System B-10 μm PRP-1 4.6 cm X10 cm cartridge (Hamilton) in a Brownlee MPLC holder; flow rate 2 ml/min; solvent A 0.1M disodium hydrogen phosphate (pH9); solvent B 95% acetonitrile, 5% water; initial conditions 100%A; upon injection a 10 min. linear gradient to 70%A, 30%B was applied followed by a 5 min. hold followed by return to initial conditions over 1 min. and a subsequent hold at initial conditions for 4 min.

The compound numbers, i.e. VII, VIII, IX, X, XII used herein refer to the reaction scheme presented above.

EXAMPLE 1

Preparation of
N-(2-Aminoethyl)-2-triphenylmethylthioacetamide
VII)

To a solution of N-(2-aminoethyl)-2-mercaptoacetamide, as described by Atkinson et al., *J.Med.Chem.* 8:29 (1965), (14.56 g, 0.11 mol) in trifluoroacetic acid (100 ml) was added triphenylmethanol (28.25 g, 0.11 mol). The resulting brown solution was stirred for 30 min. then evaporated to give a brown oil. The latter was triturated with ether (500 ml) to give the trifluoroacetate salt of (VII) as a white solid which was filtered off, washed with ether and dried, yield 49.5 g, 93%.

The trifluoroacetate salt of (VII) (10.06 g, 20.5 mmol) was partitioned between 1M aq. NaOH (30 ml, 30 mmol) and ethyl acetate. The organic phase was washed with water and saturated brine, dried ($K_2CO_3$) and evaporated to a gum which was crystallized from ethyl acetate to give (VII) (7.42 g, 96%). A second recrystallization from ethyl acetate gave analytically pure material.

Mp: 130°–132° C.

Anal. Calcd for $C_{23}H_{24}N_2OS$: C, 73.37; H, 6.42; N, 7.44; S, 8.52. Found: C, 73.11; H 6.49; N, 7.31; S, 8.46.

IR: $\nu_{max}$ 3260, 3090, 3080, 3050, 1630, 1550, 1485, 1440, 760, 750, 740, 695 cm$^{-1}$.

$^1$HNMR 270 MHz: δ1.13 (or s, 2H, $NH_2$), 2.63 (3 line m, 2H, $CH_2N$), 2.99 (4 line m, 2H, $CH_2N$), 3.13 (s, 2H, $SCH_2CO$), 6.36 (m, 1H, NH), 7.1–7.5 (m, 15H, aryl).

Preparation of 2-Benzoylthioacetic acid (VIII)

Compound (VIII) was prepared in 95% yield by Schotten-Baumann benzoylation of distilled mercaptoacetic acid.

MP 103°–105° C. (Rimpler, Chem.Ber. 99:1528 (1966):106° C.).

Electronic Spectrum (dioxan): $\nu_{max}$ 264 (8100).

IR: $\lambda_{max}$ 3000, 1710, 1665, 1300, 1205, 1170, 920, 775, 680, 645 cm$^{-1}$.

$^1$HNMR: 3.93 (s, 2H, $CH_2$), 7.48 (m, 3H, m, p-aryl), 7.92 (Abqm $J_{AB}$=2 Hz, 2H, O-aryl), 10.48 (s, 1H, COOH).

Preparation of
N,N'-Ethylene-bis(2-triphenylmethylthio)(2'-benzoylthio)acetamide(IX)

To a cooled solution of amine (VII) (3.59 g, 9.53 mmol), acid (VIII) (1.87 g, 9.54 mmol) and N-hydroxysuccinimide (1.11 g, 9.65 mmol) in $CH_2Cl_2$ (100 ml) was added a solution of DCC (2.25 g, 10.92 mmol) in $CH_2Cl_2$ (10 ml) such that the temperature remained below −5° C. After 15 min. the cooling bath was removed and the reaction was allowed to stir at room temperature for 2 h. The DCU was filtered off and washed with $CH_2Cl_2$. The combined filtrate and washings were washed with 5% aq. $NaHCO_3$, 1M aq $KHSO_4$, water and saturated brine, dried with $MgSO_4$, filtered and evaporated to a solid. Chromatography (MPLC, 1–5% $CH_3OH/CH_2Cl_2$) and recrystallization from $CH_2Cl_2$ gave (IX), yield 4..077 g (77%).

MP: 133°–135° C.

Anal. Calcd for $C_{32}H_{30}N_2O_3S_2$: C, 69.29; H, 5.45; N, 5.05; S, 11.56. Found: C, 69.10; H, 5.50; N, 5.00; S, 11.55.

Electronic spectrum (dioxan): $\lambda_{max}$ 264 (8800).

IR: $\nu_{max}$ 3280, 3080, 3060, 1650, 1550, 1450, 1210, 930, 740, 700, 670 cm$^{-1}$.

$^1$HNMR 250 MHz: δ3.04 (s, 2H, $CH_2STr$), 2.9–3.2 (m, 2H, $CH_2CH_2$), 3.66 (s, 2H, $CH_2SBz$), 6.41 (m, 1H, NH), 6.93 (m, 1H, NHO, 7.1–8.0 (m, 20H, aryl).

Preparation of
N,N'-Ethylene-bis(2-mercapto)(2'-triphenylmethylthio)acetamide(X)

A solution of benzoyl derivative (IX) (4.96 g, 8.95 mmol) in 0.1M methanolic sodium methoxide (90 ml, 9.0 mmol) was stirred for 20 min, diluted with water (150 ml) and neutralized with 1M aq. HCl to give (X) as a white solid which was filtered off, washed well with water and ether and dried, yield 3.67 g (91%).

MP: 170°–172° C.

Anal. Calcd for $C_{25}H_{26}N_2O_2S_2$: C, 66.64; H, 5.82; N, 6.22; S, 14.23. Found: C, 66.59; H, 5.86; N, 6.16; S, 14.21.

IR: $\nu_{max}$ 3260, 3080, 3060, 1655, 1570, 1445, 1230, 745, 700, 694 cm$^{-1}$.

$^1$HNMR 250 MHz: δ1.86 (tr, J=9 Hz, 1H, SH), 2.9–3.5 (m, 6H, $COCH_2SH$ and $CH_2CH_2$), 3.13 (s, 2H, $COCH_2STr$), 6.36 (m, 1H, NH), 7.07 (m, 1H, NH), 7.0–7.9 (m, 15H, aryl).

Preparation of
N,N'-Ethylenebis(2-triphenylinethylthio)[2'-(16-carpoxyhexadecyl)thio]=acetamide (XI)

To a solution of thiol (X) (1.84 g, 4.1 mmol) in 0.1M methanolic sodium methoxide (82 ml, 8.2 mmol) was added 16-bromohexadecanoic acid, as described by Chuit et al., Helv.Chim.Acta. 12:463 (1929), (1.34 g, 4.0 mmol). The resulting solutions was refluxed for 2 hrs, then acidified with 1M aq. HCl (11 ml, 11 mmol). The mixture was concentrated by evaporation and then poured into 100 ml water. The precipitate was filtered off, washed with water and dried to give 2.09 g (74%). the product was recrystallized from hot ethyl acetate to give 1.21 g (43%) of (XI).

$^1$HNMR 270 MHz (DMSO-$d_6$) δ1.23 (br s, 22H, $(CH_2)_{11}$), 1.48 (m, 4H, $CH_2CH_2COO$ and $CH_2CH_2S$), 2.18 (tr, J=7 Hz, 2H, $\overline{CH_2}COO$) 2.50 (tr, J=7 Hz, 2H, $CH_2S$), 2.77 (s, 2H, $\overline{CH_2}CO$), 3.04 (br s, 6H, $CH_2CH_2$ and $CH_2CO$), 7.33 (m, 15H, aryl), 7.95 (m, 2H, $\overline{NHx2}$), 11.98 (m, 1H, COOH).

Preparation of
N,N'-Ethylenebis(2-mercapto)[2'-(16-carboxyhexadecyl)thio]acetamide (XII), i.e. (Hexadec)ema A solution of triphenylmethyl derivative (XI) (1.39 g, 1.97 mm) in trifluoroacetic acid (10 ml) was treated with triethylsilane (0.35 ml, 2.20 mmol) causing immediate color discharge and precipitation of triphenylmethane. The addition of hexanes (20 ml) and water (20 ml) gave a slurry which was filtered off, washed well with water and hexanes and recrystallized from hot methanol to give (XII), yield 0.64 g, 71%.

$^1$HNMR 270 MHz (DMSO-d): 1.24 (br s, 22H, $(CH_2)_{11}$), 1.48 (m, 4H, $CH_2CH_2COO$ and $CH_2CH_2$ S), 2.18 (br, J=7 Hz, 2H, $\overline{CH_2}COO$), 2.53 (br, J=7 Hz, 2H, $CH_2S$), 3.07 (s, 4H, $CO\overline{CH_2}$) 3.11 (m, 4H, $CH_2CH_2$, 8.04 (m, 2H, NH x 2), 11.95 (br s, 1H, $COO\overline{H}$).

EXAMPLE 2

Preparation of
$^{99}$Tc-Oxo[N,N'-ethylenebis(2-mercapto)[2'(16-carboxy hexadecyl)thiol]acetamidotechnetium (+5), i.e. 99-TcO (Hexadec)ema To warm methanolic solution of ligand XII (17 mg, 0.037 mmol in 1.0 ml) was added a purple methanolic solution of sodium oxobis(1,2-ethanediolato)technetate (10 mg, 0.039 mmol in 1.0 ml) to give a slightly cloudy orange solution. An aliquot filtered through a 0.22 μm filter, was analysed by HPLC (system A) an showed two peaks for the isomeric technetium complexes $R_T$ 14.7 min. (90%) and $R_T$ 15.9 min 7%).

EXAMPLE 3

Preparation of $^{99m}$TcO(Hexadec)ema

A Glucoscan ™ kit (available from NEN Products Division, E. I. duPont de Nemours & Company) is reconstituted with $^{99m}TcO_4^{-1}$ generator eluate (40 mCi in 2 cc) and let stand for 5 min. at room temperature. (Hexadec)ema from Example 1 (10 mg) is dissolved in 0.05M NaOH (1 cc) with gentle warming. A 0.5 cc (10 mCi) aliquot of the $^{99m}$Tc-glucoheptonate solution is added to the ligand solution, the reaction mixture is stirred for 5 min. and then 0.05M HCl (approx. 0.8 cc) is added to just above the cloud point (pH approx. 9). The solution is filtered through a 0.22 μm Millex ™ GV filter and an aliquot is assayed by HPLC. To the bulk solution is added fatty acid free human serum albumin (100 mg, Sigma) and the mixture is stirred until the albumin is dissolved. Several drops of 0.05M HCl are added to give a solution at pH 7. The slightly cloudy solution is then diluted with 0.9% saline (2 cc) and refiltered through a 0.22 μm Millex ™ GV into a serum vial.

The invention has been described in detail with reference to the preferred embodiments thereof. However, it will be appreciated that those skilled in the art, upon consideration of this disclosure may make modifications and improvements within the spirit and scope of this invention.

What is claimed is:

1. Compounds useful for forming technetium-99m radioimaging agents having the structural formulae:

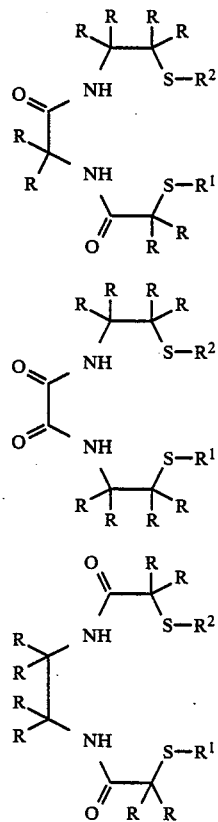

wherein each R is independently selected from hydrogen, substituted or unsubstituted lower alkyl, substituted or unsubstituted lower alkoxy, or COR$^4$ wherein R$^4$ is selected from substituted or unsubstituted lower alkoxy; or two R's can be taken together to form a lower alkylidene or hydrocarbon ring; one of R$^1$ or R$^2$ is selected from hydrogen or a thiol protecting group; the other of R$^1$ or R$^2$ is a C$_{14}$ to C$_{24}$ fatty acid group; and pharmaceutically acceptable salts thereof.

2. The compounds of claim 1, wherein R$^1$ or R$^2$ is a C$_{15}$ to C$_{20}$ fatty acid moiety.

3. The compounds of claim 1, wherein R$^1$ or R$^2$ is a C$_{16}$ to C$_{18}$ fatty acid moiety.

4. A complex formed by reacting a compound of claim 1 with technetium in the presence of a reducing agent.

5. The complex of claim 4, wherein said reducing agent is selected from a dithionite group, a stannous ion, or a ferrous ion.

6. A complex formed by labelling a compound of claim 1 with technetium-99m.

7. A complex formed by labelling a compound of claim 1 with technetium by ligand exchange with a prereduced technetium complex.

8. A compound of claim 2, wherein R$^1$ or R$^2$ is selected from acetamidomethyl, loweralkylaminocarbonyl, loweralkanoylaminomethyl, aroylaminomethyl, t-butyl, arylmethyl, aroyl, aryloxycarbonyl, or loweralkoxy carbonyl.

9. A compound of claim 8, wherein R$^1$ or R$^2$ is acetamidomethyl.

10. A technetium complex having the structural formula:

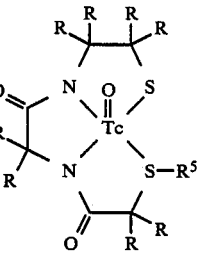

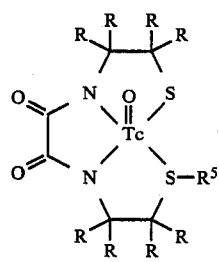

or

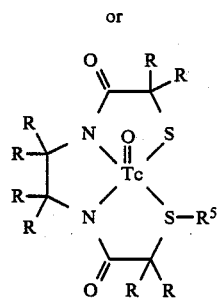

wherein each R is independently selected from hydrogen, substituted or unsubstituted lower alkyl, substituted or unsubstituted lower alkoxy, or COR$^4$ wherein R$^4$ is selected from substituted or unsubstituted lower alkoxy; or two R's can be taken together to form a lower akylidene group or a hydrocarbon ring; and R$^5$ is a C$_{12}$ to C$_{24}$ fatty acid group;

and pharmaceutically acceptable salts thereof.

11. A kit for preparing a radiopharmaceutical preparation, said kit comprising a sealed vial containing a predetermined quantity of a compound of claim 1 and a sufficient amount of reducing agent to label said compound with technetium.

12. The kit of claim 11, wherein $R^1$ or $R^2$ is selected from acetamidomethyl, benzoyl, diphenylmethyl, ethyl aminocarbonyl, t-butyl or trityl.

13. The kit of claim 12, wherein $R^1$ or $R^2$ is acetamidomethyl.

14. The kit of claim 11, wherein said reducing agent is selected from a dithionite group, a stannous ion, or a ferrous ion.

15. A kit for preparing a radiopharmaceutical preparation, said kit comprising a sterilized, sealed vial comprising a lyophilized admixture of a reducing agent for technetium, and a compound of claim 1, capable of forming a pentacoordinate oxotechnetium complex in an aqueous solution.

16. The kit of claim 15, wherein said reducing agent is selected from a dithionite group, a stannous ion, or a ferrous ion.

17. The kit of claim 16, wherein said reducing agent is stannous chloride.

18. A method for diagnosing myocardial disfunction in a mammal, said method comprising injecting into said mammal a technetium complex of claim 10, in a suitable pharmacological carrier; and scanning the myocardial system of said mammal using radioscintigraphic imaging apparatus.

19. Compounds useful for forming technetium-99m radioimaging agents having the structural formulae:

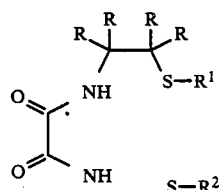
(A)

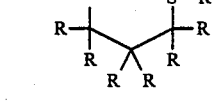
(B)

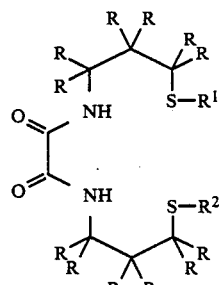
(C)

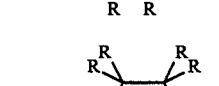
(D)

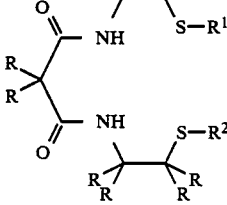

-continued

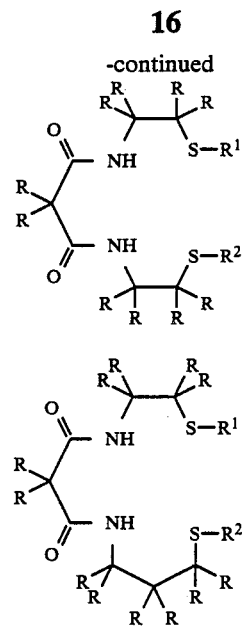
(D)

(D)

(E)

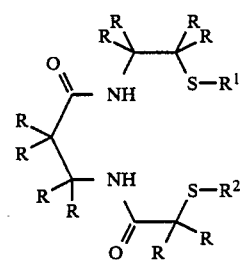
(F)

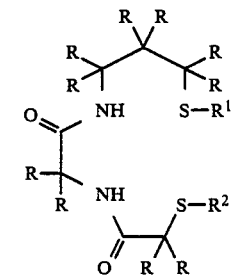
(G)

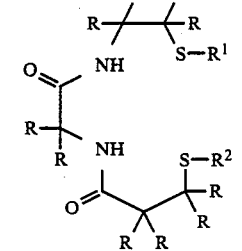
(H)

-continued

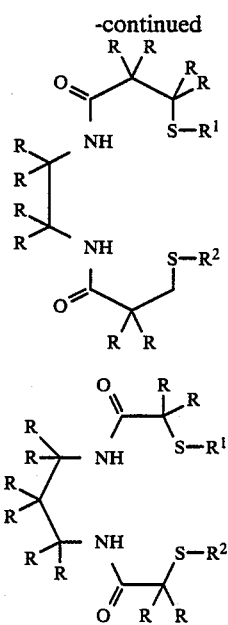

(J)

(K)

wherein each R is independently selected from hydrogen, substituted or unsubstituted lower alkyl, substituted or unsubstituted lower alkoxy, or $COR^4$ wherein $R^4$ is selected from substituted or unsubstituted lower alkoxy; or two R's can be taken together to form a lower alkylidene group or a hydrocarbon ring; one of $R^1$ or $R^2$ is selected from hydrogen or a thiol protecting group; the other of $R^1$ or $R^2$ is a $C_{14}$ to $C_{24}$ fatty acid group:

and pharmaceutically acceptable salts thereof.

20. A complex formed by reacting a compound of claim 19 with technetium in the presence of a reducing agent.

21. A complex formed by labelling a compound of claim 19 with technetium-99m.

22. A complex formed by labelling a compound of claim 19 with technetium by ligand exchange with a prereduced technetium complex.

23. A compound of claim 19, wherein $R^1$ or $R^2$ is selected from acetamidomethyl, benzoyl, diphenylmethyl, ethylaminocarbonyl, t-butyl or trityl.

24. A compound of claim 23, wherein $R^1$ or $R^2$ is acetamidomethyl.

25. A kit for preparing a radiopharmaceutical preparation, said kit comprising a sealed vial containing a predetermined quantity of a compound of claim 19 and a sufficient amount of reducing agent to label said compound with technetium.

26. The kit of claim 25, wherein said reducing agent is a stannous ion.

27. The kit of claim 26, wherein said compound and said reducing agent are lyophilized in a sterile vial and said compound is capable of forming a pentacoordinate oxotechnetium complex in an aqueous solution.

* * * * *